United States Patent
Ellegård et al.

(10) Patent No.: US 9,689,011 B2
(45) Date of Patent: Jun. 27, 2017

(54) METHOD FOR THE MANUFACTURE OF BIO-PRODUCTS WITH A MODIFIED SUGAR PROFILE

(71) Applicant: Hamlet Protein A/S, Horsens (DK)

(72) Inventors: Katrine Hvid Ellegård, Ry (DK); Karl Kristian Thomsen, Horsens (DK); Ole Kaae Hansen, Egå (DK)

(73) Assignee: HAMLET PROTEIN A/S, Horsens (DK)

( * ) Notice: Subject to any disclaimer, the term of this patent is extended or adjusted under 35 U.S.C. 154(b) by 0 days.

(21) Appl. No.: 14/400,891

(22) PCT Filed: May 15, 2013

(86) PCT No.: PCT/EP2013/060025
§ 371 (c)(1),
(2) Date: Nov. 13, 2014

(87) PCT Pub. No.: WO2013/171259
PCT Pub. Date: Nov. 21, 2013

(65) Prior Publication Data
US 2015/0141524 A1    May 21, 2015

Related U.S. Application Data

(60) Provisional application No. 61/647,667, filed on May 16, 2012, provisional application No. 61/777,938, filed on Mar. 12, 2013.

(30) Foreign Application Priority Data

May 16, 2012 (EP) ..................... 12168274

(51) Int. Cl.
| | | |
|---|---|---|
| C12P 19/02 | (2006.01) | |
| C12P 19/12 | (2006.01) | |
| A23L 11/30 | (2016.01) | |
| C12P 19/14 | (2006.01) | |

(52) U.S. Cl.
CPC ............... *C12P 19/14* (2013.01); *A23L 11/30* (2016.08); *C12P 19/02* (2013.01); *C12P 19/12* (2013.01)

(58) Field of Classification Search
None
See application file for complete search history.

(56) References Cited

U.S. PATENT DOCUMENTS

| | | |
|---|---|---|
| 3,632,346 A | 1/1972 | Sherba |
| 8,153,174 B2 | 4/2012 | Hansen |

FOREIGN PATENT DOCUMENTS

| | | |
|---|---|---|
| JP | 2005-224133 A | 8/2005 |
| SU | 1 368 182 A1 | 1/1988 |
| WO | WO 2006/102907 A1 | 10/2006 |
| WO | WO 2009/143591 A2 | 12/2009 |

OTHER PUBLICATIONS

International Search Report issued in application No. PCT/EP2013/060025 on Nov. 25, 2013.
Zhang et al., "The methods of using α-galactosidase," Enzyme Preparation Industry, vol. 2, p. 791, Jun. 1998.
He et al., "α-Galactosidase," Food Fermentation and Brewing Technology, pp. 279-281, Aug. 2011.
Japanese Office Action issued on Oct. 11, 2016 in application No. JP 201380023280.1.

*Primary Examiner* — Suzanne M Noakes
*Assistant Examiner* — Stephen Chong
(74) *Attorney, Agent, or Firm* — Foley & Lardner LLP

(57) ABSTRACT

The invention relates to a method for the production of a solid bio-product wherein at least 80% of the original indigestible oligosaccharide (raffinose, stachyose and verbascose) content has been degraded into digestible mono- and disaccharides, comprising the following steps: 1) providing a mixture of milled or flaked or otherwise disintegrated biomass, comprising oligosaccharides and optionally polysaccharides and further comprising proteinaceous plant parts, water and one or more enzyme preparations containing α-galactosidase(s); 2) reacting the mixture resulting from step (1) under continuous mixing and under conditions where the water content in the initial mixture does not exceed 65% by weight, for 0.15-36 hours at a temperature of about 20-65° C.; 3) incubating the reacted mixture from step (2) at a temperature and in a time period which inactivate said α-galactosidase(s), as well as solid bio-products obtainable by such method. The invention further relates to uses of the bio-product and a food, a feed, a cosmetic or pharmaceutical product or a nutritional supplement containing the solid bio-product.

22 Claims, No Drawings

METHOD FOR THE MANUFACTURE OF BIO-PRODUCTS WITH A MODIFIED SUGAR PROFILE

FIELD OF THE INVENTION

The present invention relates to a method for the production of bio-products with a modified sugar profile that is enriched in monosaccharide and sucrose content and reduced in indigestible oligosaccharide content. Further the present invention relates to a method, where the fermentable sugars originally present or provided by α-galactosidase, may be further converted with a fungus or bacteria.

Furthermore it relates to the products obtainable by the method as well as the use of the products obtained.

BACKGROUND OF THE INVENTION

There is a need for bio-products that primarily can be used as ingredients in food or feed. The basic constituents in such products are proteins, fats and carbohydrates.

Suitable biomasses for such products are grasses and oil bearing crops, such as seeds, cereals and pulses. Cereals have a protein content up to 15% e.g. wheat, and pulses have a content of up to 45% e.g. soybeans, based on dry matter.

A general problem especially related to pulses is the content of indigestible oligosaccharides causing flatulence when fermented in the gut. The presence of the oligosaccharides raffinose, stachyose and verbascose can be reduced by soaking in water or enzymatically by hydrolysis with α-galactosidase. The problem associated with this is that it adds to the cost of the final product due to the use of water in soaking or by an enzymatic treatment that has to be performed at a relatively high water content of 80% or more.

U.S. Pat. No. 6,238,725 B1 discloses a method for preparing a legume where the flatulence-causing oligosaccharides are removed by soaking in water.

WO 02/15712 A2 discloses a method for manufacturing a soy protein product by the use of α-galactosidase where the water content in the process is 80-90%. The soy product obtained has a protein content of min. 60% and a total content of raffinose and stachyose of less than 5%.

US 2003/019041 A1 discloses a method for the manufacture of a soy protein concentrate by the use of a glycosidase enzyme (α-galactosidase) where the water content in the process according to the examples is approx. 90%. After hydrolysis carbohydrates and salts are removed by ultrafiltration. The soy concentrate obtained has a protein content of min. 65% and a combined content of raffinose and stachyose of less than 4%.

WO 2009/143591 discloses a method for processing soybeans by the use of enzyme(s) which is capable of converting the insoluble polysaccharides into soluble sugars and hydrolyzing the proteins at a water content of maximally 35%. The level of degradation is not disclosed.

The object of the present invention is to provide an improved method for the production of bio-products with a modified sugar profile that is enriched in monosaccharide and sucrose content and reduced in indigestible oligosaccharide content, which can be performed at lower costs due to the low water content in the process.

Yet another object is to provide a method where the fermentable sugars originally present or provided by α-galactosidase, may be further converted with a fungus e.g. yeasts and/or bacteria e.g. *Lactobacillus*.

These objects are fulfilled with the process and the products of the present invention.

SUMMARY OF THE INVENTION

Accordingly, the present invention relates to a method for the production of a solid bio-product wherein at least 80% of the original plant indigestible oligosaccharide (raffinose, stachyose and verbascose) content has been degraded into digestible mono- and disaccharides comprising the following steps:
1) providing a mixture of milled or flaked or otherwise disintegrated biomass, comprising oligosaccharides and optionally polysaccharides, and further comprising proteinaceous plant parts, water and one or more enzyme preparations containing α-galactosidase(s);
2) reacting the mixture resulting from step (1) under continuous mixing and under conditions where the water content in the initial mixture does not exceed 65% by weight, for 0.15-36 hours at a temperature of about 20-65° C.;
3) incubating the reacted mixture from step (2) at a temperature and in a time period which inactivate said α-galactosidase(s).

It is surprising that the enzymatic hydrolysis i.e. catalytic decomposition by reaction with water can be performed at a water content that does not exceed 65% by weight. Normally the low content of water tends to slow down the reaction due to mechanical contact problems with the substrate. To give a scientific explanation at this stage would be speculative. The combination of pre-treatment of the substrate, the activity of the α-galactosidase and the mixing procedure during the reaction is believed to be the key factors.

The benefit is that the product resulting from the method only contains minor amounts of water due to the low water content during the process, and accordingly, drying of the product can be performed at low costs due to the minor amount of water to be removed.

The invention further provides a solid bio-product obtainable by a process according to the invention comprising plant proteins in an amount up to about 60% and optionally glycerides up to 25% by weight of dry matter.

The invention also provides a solid bio-product obtainable by a process as defined in the claims 13-20.

Finally, the invention provides a food, feed, cosmetic or pharmaceutical product or a nutritional supplement containing from 1 to 99% by weight of a solid bio-product according to the invention.

DEFINITIONS

In the context of the current invention, the following terms are meant to comprise the following, unless defined elsewhere in the description.

The terms "about", "around", "approximately", or "~" are meant to indicate e.g. the measuring uncertainty commonly experienced in the art, which can be in the order of magnitude of e.g. +/−1, 2, 5, 10, 20, or even 50%.

The term "comprising" is to be interpreted as specifying the presence of the stated part(s), step(s), feature(s), composition(s), chemical(s), or component(s), but does not exclude the presence of one or more additional parts, steps, features, compositions, chemicals or components. E.g., a composition comprising a chemical compound may thus comprise additional chemical compounds, etc.

The term indigestible is to be interpreted as not digestible by humans and monogastric/non-ruminant animals.

The term "at least 80% of the original indigestible oligosaccharide content has been degraded" is to be interpreted as specifying that the total content of indigestible oligosaccharides has been degraded by at least 80% and also includes products wherein one type of oligosaccharide may be degraded to a larger extent than another type of oligosaccharide, and even wherein one type of oligosaccharide may be degraded only in a minor extent, as long as the total content of the original—starting—oligosaccharides has been reduced as specified by at least 80%.

Biomass:

Comprises biological material produced by the photosynthesis and that can be used as raw material in industrial production.

In this context, biomass refers to plant matter in the form of grasses, cereals, seeds, nuts, beans and peas, etc., and mixtures thereof.

Furthermore a biomass comprising pulses is preferred due to the protein content and composition. They also contain carbohydrates comprising alpha-galactosides. In general the principal alpha-galactoside is stachyose except in field pea where the principal oligosaccharide is verbascose.

Otherwise Disintegrated:

Means disintegrated by cooking and/or by maceration and/or acid or alkaline pressure-cooking, or ultrasonic treatment.

Carbohydrates:

Comprise mono-, di-, oligo- and polysaccharides.

C5 sugars (pentoses) are carbohydrates where the component monomer sugars are composed of a ring with five carbon atoms e.g. arabinose.

C6 sugars (hexoses) are carbohydrates where the component monomer sugars are composed of a ring with six carbon atoms e.g. galactose.

Oligosaccharides and Polysaccharides:

An oligosaccharide is a saccharide polymer containing a small number (including up to e.g. 8-10) of component monomer sugars, also known as simple sugars. Typical examples are the trisaccharide raffinose (D-galactose-α1,6-D-glucose-α1,β2-D-fructose), the tetrasaccharide stachyose (D-galactose-α1,6-D-galactose-α1,6-D-glucose-α1,β2-D-fructose) and the pentasaccharide verbascose (D-galactose-α1,6-D-galactose-α1,6-D-galactose-α1,6-D-glucose-α1,β2-D-fructose).

Polysaccharides are saccharide polymers containing a large number of component monomer sugars, also known as complex carbohydrates. If the monomer sugars are of the same type the polysaccharide is called a homopolysaccharide, but when more than one type is present they are called heteropolysaccharides.

Examples include storage polysaccharides such as starch and structural polysaccharides such as cellulose and arabinoxylan.

Proteinaceous Materials:

Comprise organic compounds made of amino acids arranged in a linear chain and joined together by a bond called a peptide bond. At a chain length of up to approximately 50 amino acids the compound is called a peptide; at higher molecular weight the organic compound is called a polypeptide or a protein.

Fats:

Comprise esters between fatty acids and glycerol. One molecule of glycerol can be esterified to one, two and tree fatty acid molecules resulting in a monoglyceride, a diglyceride or a triglyceride respectively. Usually fats consist of mainly triglycerides and minor amounts of lecithins, sterols, etc. If the fat is liquid at room temperature it is normally called oil. With respect to oils, fats and related products in this context, reference is made to "Lipid Glossary 2", F. D. Gunstone, The Oily Press, 2004.

Glycerides:

Comprise mono-, di- and triglycerides.

Processing Aids:

1. Enzymes

Enzyme(s) is a very large class of protein substances that act as catalysts. Commonly, they are divided in six classes, and the main classes falling within the scope of this invention can be transferases that transfer functional groups and the hydrolases that hydrolyze various bonds.

In this context glycoside hydrolase enzymes are important and especially α-galactosidase(s) that is an enzyme that hydrolyses the terminal alpha-galactose in alpha-galactosides, comprising galactose oligosaccharides and galactomannans, liberating D-galactose residues.

The activity of α-galactosidase in a preparation is expressed in units/g of actual enzyme product and assayed by reacting p-nitrophenyl-α-D-galactopyranoside with water and enzyme for 10 min at 25° C. to form D-galactose and p-nitrophenyl that is monitored spectrophotometrically at 410 nm.

One α-galactosidase unit is the enzymatic activity that liberates one micromole ($10^{-6}$ mole) of p-nitrophenyl per minute.

Further examples of enzymes comprise: protease(s), peptidase(s), β-galactosidase(s), amylase(s), glucanase(s), pectinase(s), hemicellulase(s), phytase(s), lipase(s), phospholipase(s) and oxido-reductase(s).

2. Plant Components and Organic Processing Agents

Some of the functional properties that are important in this context are: Antioxidant, anti-bacterial action, wetting properties and stimulation of enzymes.

The list of plant-based components is huge, but the most important are the following: Rosemary, thyme, oregano, flavonoids, phenolic acids, saponins and α- and β-acids from hops e.g. from humulone and lupolone, for the modulation of soluble carbohydrates. Furthermore organic acids e.g. Sorbic-, propionic-, lactic-, citric- and ascorbic acid and their salts for the adjustment of the pH-value, preservation and chelating properties is part of this group of processing aids.

3. Inorganic Processing Agents

Comprise inorganic compositions that are able to preserve the fermenting mixture against bacterial attack during processing e.g. Sodium bisulfite, etc.

Anticaking and flow improving agents in the final product e.g. Potassium aluminum silicate, etc.

Processed Food Products:

Comprise dairy products, processed meat products, sweets, desserts, ice cream desserts, canned products; freeze dried meals, dressings, soups, convenience food, bread, cakes, etc.

Processed Feed Products:

Comprise ready-to-use feed or feed ingredients for animals such as piglets, calves, poultry, furred animals, sheep, cats, dogs, fish and crustaceans, etc.

Pharmaceutical Products:

Comprise products, typically in the form of a tablet or in granulated form, containing one or more biologically active ingredients intended for curing and/or alleviating the symptoms of a disease or a condition. Pharmaceutical products furthermore comprise pharmaceutically acceptable excipients and/or carriers. The solid bio products herein disclosed are very well suited for use as a pharmaceutically acceptable ingredient in a tablet or granulate.

Cosmetic Products:

Comprise products intended for personal hygiene as well as improved appearance such as conditioners and bath preparations.

DETAILED DESCRIPTION OF THE INVENTION

The original plant indigestible oligosaccharides the content of which is degraded by the process of the invention are primarily raffinose, stachyose, and verbascose.

The water content in the initial reaction mixture does not exceed 65% by weight, which implies that the dry matter content in the mixture is at least 35%.

The reaction time is 0.15-36 hours at a temperature of about 20-65° C. The temperature may e.g. vary from 25-60° C., 30-55° C., from 35 to 50° C., from 40 to 45° C.; the reaction time may e.g. vary from 10 minutes to 36 hours, from 20 minutes to 30 hours, from 1 to 24 hours, from 2 to 20 hours, from 4 to 18 hours, from 8 to 16 hours or from 12 to 14 hours.

In one embodiment of the method of the invention it further comprises that fungus, such as live yeast, and/or bacteria is added to the biomass comprising oligosaccharides and/or polysaccharides and proteinaceous plant parts in a dry matter ratio between fungus/bacteria and biomass of from 1:2 to 1:400, and that the incubating in step (3) is carried out at a temperature and in a time period which inactivate said α-galactosidase(s) and fungus and/or bacteria. Thus dry matter ratios such as: 1:2; 1:3; 1:4; 1:5; 1:6; 1:7; 1:8; 1:9; 1:10; 1:20; 1:30; 1:40; 1:50; 1:60; 1:70; 1:80; 1:90; 1:100, 1:200 and 1:300 are included. The incubation of the reacted mixture may be carried out at about 70-150° C., e.g. 85-150° C., including 70, 75, 80, 85, 86, 87, 88, 89, 90, 91, 92, 93, 94, 95, 96, 97, 98, 99, 100, 105, 110, 115, 120, 125, 130, 135, 140, 145, 150° C. for 0.5-240 minutes, e.g. 6-240 minutes, including 0.5, 1, 2, 3, 4, 5, 6, 7, 8, 9, 10, 15, 20, 25, 30, 35, 40, 45, 50, 55, 60, 90, 120, 150, 180, 210, and 240 minutes.

When choosing conditions for the incubation the skilled person knows that when using very high temperatures, relatively short incubation times are needed.

In this embodiment the reacting step (2) may be performed under anaerobic and/or aerobic conditions.

In a second embodiment the amount of the α-galactosidase preparation(s) is from 0.001 to 1.0% by weight of the biomass in the initial mixture where the α-galactosidase preparation(s) is having an activity of 5,000 α-galactosidase units/g enzyme product, and/or the reaction in step (2) is performed under conditions where the water content in the initial mixture is from 30 to 65% by weight, which implies that the dry matter content in the mixture is from 35 to 70 by weight %.

Thus, the water content may vary to be e.g. from 35 to 60%, from 40 to 55% or from 45 to 50%. Hence, the dry matter content in the reaction mixture provided in step (1) may vary correspondingly to be e.g. from 40 to 65%, from 45 to 60% or from 50 to 55%, e.g. be 45%, 50, %, 55%, 57.5%, 60%, 62.5%, 65% or 67.5%.

The amount of the one or more α-galactosidase preparation(s) may vary e.g. from 0.01 to 1.0%, from 0.025 to 0.75%, from 0.05 to 0.5%, from 0.075 to 0.25% or from 0.1 to 0.125% of an α-galactosidase preparation(s) having an activity of 5,000 α-galactosidase units/g enzyme product. The activity of the α-galactosidase preparation(s) may also be lower or higher than 5,000 α-galactosidase units/g enzyme product, e.g. from 5 to 200,000, or from 100,000 to 150,000, 50 to 50,000 or from 500 to 10,000 units/g enzyme product, as long as the amount of enzyme applied is adapted to the strength of the enzyme product. The higher the amount and activity of the α-galactosidase preparation the lower reaction time is generally needed and vice versa. The skilled person within enzyme technology will be aware of this.

In a third embodiment the reaction in step (2) is performed in one or more non-vertical, interconnected paddle worm or continuous worm conveyers with inlet means for the reaction mixture and additives and outlet means for the product as well as control means for rotation speed, temperature and pH. This embodiment may be a variant wherein the continuous worm conveyer can be an optionally modified type of a single bladed or multi bladed screw or intersected screw conveyer designed to transport the reacting mixture and at the same time lifting the material so that it is transported and agitated without compacting it. The reaction step (2) may also be performed in a Vertical Screw Mixer, e.g. a Nauta Mixer.

In a forth embodiment of the method of the invention one or more processing aids, such as hop products containing α- and β-acids from hops, are added in any of steps (1), (2) and/or (3). The one or more processing aids may also be an enzyme, a plant component and/or organic processing agent and/or inorganic processing agent as defined above in the definition section of the present application.

In a fifth embodiment the fungus and/or bacteria that may be added to the biomass is live yeast selected among *Saccharomyces cerevisiae* strains, including spent brewer's yeast and spent distiller's yeast and spent yeast from wine production and baker's yeast, as well as *Bacillus cereus* strains and yeast strains fermenting C5 sugars. The live yeast may e.g. be added in an amount of from 0.25 to 10%, such as 0.5%, 1%, 1.5%, 2%, 2.5%, 3%, 3.5%, 4%, 4.5, 5%, 6%, 7%, 8% or 9.

The proteinaceous plant parts comprised in the biomass may in a $6^{th}$ embodiment be pulses, such as soy, pea, bean, lupine, and/or cereals, such as wheat, and/or grasses and further be as defined in the definition section of the present application. The biomass may in a $7^{th}$ embodiment further comprise oils and fats, e.g. from seeds of oil bearing plants, e.g. rape seed and soy, and further as defined above in the definition section of the present application.

In an $8^{th}$ embodiment the reaction mixture resulting from step (3) is dried to a water content of no more than 10% by weight.

In further embodiments the amount of said one or more α-galactosidase preparation(s) is from 0.25 to 1.0% by weight of the dry matter of the biomass in the initial mixture where the α-galactosidase preparation is having an activity of 5,000 α-galactosidase units pr. g of enzyme product, and said reacting in step (2) is performed for 4-36 hours at a temperature of 30-60° C.; or the amount of said one or more α-galactosidase preparation(s) is from 0.25 to 1.0% by weight of the dry matter of the biomass in the initial mixture where the α-galactosidase preparation is having an activity of 5,000 α-galactosidase units pr. g of enzyme product, and said reacting in step (2) is performed for 4-36 hours at a temperature of 50-60° C.; or the amount of said one or more α-galactosidase preparation(s) is from 0.01 to 1.0% by weight of the dry matter of the biomass in the initial mixture where the α-galactosidase preparation is having an activity of 5,000 α-galactosidase units pr. g of enzyme product, and said reacting in step (2) is performed for 8-36 hours at a temperature 50-60° C.; or the amount of said one or more α-galactosidase preparation(s) is from 0.05 to 1.0% by weight of the dry matter of the biomass in the initial mixture where the α-galactosidase preparation is having an activity of 5,000 α-galactosidase units pr. g of enzyme product, said reacting in step (2) is performed under conditions where the water content in the initial mixture is from 40-65% and at a temperature of 50-60° C.; or fungus and/or bacteria is live yeast added in an amount of 0.25% to 10%.

In a final embodiment the method is performed as a batch, fed-batch or continuous process.

The solid bio-product obtainable by the process defined in claims 1 to 16 comprises proteins in an amount up to about 60% by weight; the amount may be less than 60%, e.g. 10-59%, 40-59%, 45-58%, 48-55% or 50-53% by weight of dry matter. The amount of glycerides may e.g. be 0-20%, 2-20%, 5-18% or 10-15% by weight of dry matter.

The solid bio-product defined in claim 22 may comprise up to about 75% protein, e.g. from 40-75%, from 45-70%, from 48 to 65%, from 50-60% or from 53-55% protein by weight. It may further comprise glycerides in an amount up to 25% by weight of dry matter, e.g. 0-20%, 2-20%, 5-18% or 10-15% by weight of dry matter.

The solid bio-product obtainable by the process of claims 11-16 may comprise up to 60% protein by weight or it may comprise more than 60% protein by weight, e.g. from 40-75%, from 45-70%, from 48 to 65%, from 50-60% or from 53-55% protein by weight. They may further comprise glycerides in an amount up to 25% by weight of dry matter, e.g. 0-20%, 2-20%, 5-18% or 10-15% by weight of dry matter.

The amount of protein can be especially high when the biomass has been fermented with live yeast according to the process of claim 2.

The oligosaccharides raffinose, stachyose and verbascose are degraded by the method of the invention to mono- and disaccharides, such as galactose and sucrose. Sucrose is an interesting product resulting of the method, because a high content of sucrose in the resulting bio-product will contribute to a satiated feeling after consumption. The amount of sucrose may be as high as 15-20% by weight of dry matter.

In one embodiment the solid bio-product of the invention comprises a total amount of raffinose, stachyose and verbascose of less than 8% by weight; e.g. less than 6%, less than 5%, less than 4%, less than 3%, less than 2 or less than 1% by weight.

In another embodiment the solid bio-product of the invention comprises a total amount of raffinose of less than 3.0%, e.g. less than 2%, less than 1.5%, less than 1% or less than 0.75% or less than 0.5% or less than 0.25%.

In yet another embodiment the solid bio-product of the invention comprises a total amount of stachyose of less than 1.0%, e.g. less than 0.75% or less than 0.5% or less than 0.25%.

The invention also relates to the use of a solid bio-product according to the invention in a processed food product for human and/or animal consumption; as an ingredient to be used in a food or feed product; or as an ingredient of a cosmetic or a pharmaceutical product or a nutritional supplement.

Finally the invention relates to a food, feed, cosmetic or pharmaceutical product or a nutritional supplement containing from 1 to 99% by weight of a solid bio-product according to the invention.

EXAMPLES

Example 1

Enzymatic Hydrolysis in a Laboratory Scale Process of a Biomass Comprising Oligosaccharides from Soy 1.1 Materials and Methods The enzymatic hydrolysis of the oligosaccharides stachyose and raffinose was performed on 10 g of a biomass of defatted soy and water containing the α-galactosidase enzyme added in an amount to reach a certain dry matter (DM) content of the mixture, and a certain enzyme concentration.

The mixing was performed to ensure homogeneity of the mixture.

The enzyme used in varying concentrations based on the dry matter of soy bean meal was a commercial product from Advanced Enzyme Technologies, Maharasthra, India, marketed under the trade name SEBSoy 5.0 L.

The activity of SEBSoy 5.0 L is standardised to 5,000 U/g.

The enzymatic hydrolysis was performed in small glass containers at 34° C. and 55° C. for 4 to 16 hours followed by heat treatment at 100° C. to inactivate the enzyme.

After the enzymatic hydrolysis was terminated the content of soluble carbohydrates was extracted by stirring a watery suspension slurry of 10% DM for 30 min followed by centrifugation for 10 min at 3,000×g.

The mono- and oligosaccharides in the watery extracts of the biomass was analyzed by thin layer chromatography on TLC silica gel 60 plates (Merck). The different components were quantified by comparison to standards of known concentration. (*Carbohydrate analysis—A practical approach*; IRL Press, Oxford. Ed. M. F. Chaplan & J. F. Kennedy, 1986).

1.2 Results 1.2-a. Dose Response at Different Temperatures

The results listed in the following table were obtained after a reaction time of 4 hours, at 45% DM:

| | Temperature 34° C. | | Temperature 55° C. | |
|---|---|---|---|---|
| Dose of SEBSoy | Stachyose | Raffinose | Stachyose | Raffinose |
| Reference | 6.0% | 2.0% | 6.0% | 2.0% |
| 0.05% | — | — | 4.0% | 3.0% |
| 0.10% | 2.5% | 3.5% | 1.5% | 2.5% |
| 0.25% | 1.5% | 3.0% | <0.25% | 0.75% |
| 0.50% | 0.25% | 1.0% | — | — |

From the results it can be seen that stachyose is reduced at lower enzyme concentrations as stachyose produce one molecule D-galactose and one molecule raffinose in the first step in the hydrolysis.

The total reduction of the combined content of stachyose and raffinose is almost a linear function of the enzyme concentration.

Furthermore it can be seen that an increase in temperature from 34° C. to 55° C. corresponds to the same effect at a dose increase by a factor of 2 to 3.

1.2-b. Effect as a Function of Reaction Time

The results listed in the following table were obtained with a dose of 0.05% SEBSoy, and at a reaction temperature of 55° C., at 45% DM:

| Reaction time In hours | Stachyose | Raffinose | Stacchyose + Raffinose |
|---|---|---|---|
| 4 | 3.50% | 4.00% | 7.50% |
| 8 | 0.75% | 2.00% | 2.75% |
| 16 | <0.25% | 0.75% | <1.00% |

From the results it can be seen that every increase of the reaction time by a factor of 2 reduces the combined content of stachyose and raffinose by a factor of almost 3.

1.2-c. Effect as a Function of Dry Matter Content in the Reaction Mixture

The results listed in the following table were obtained with a dose of 0.25% SEBSoy, and at a reaction time of 4 hours at a temperature of 55° C.:

| Dry matter in % by weight | Stachyose | Raffinose | Stacchyose + Raffinose |
|---|---|---|---|
| 50 | 0.25% | 1.00% | 1.25% |
| 55 | 0.50% | 1.25% | 1.75% |
| 60 | 0.75% | 1.50% | 2.25% |
| 65 | 1.50% | 1.75% | 3.25% |

From the results it can be seen that there is an increase in the total content of stachyose and raffinose as a function of dry matter and in the interval 50 to 60% the increase is equidistant.

Example 2

Enzymatic Hydrolysis in a Laboratory Scale Process of a Biomass Comprising Oligosaccharides from Peas

2.1 Materials and Methods

The enzymatic hydrolysis of the oligosaccharides stachyose, raffinose and verbascose was performed on 10 g of a biomass of milled pea and water containing the α-galactosidase enzyme added in an amount to reach a dry matter (DM) content of the mixture of 50%, and a certain enzyme concentration.

The enzyme preparation and the method used was as described in Example 1 under paragraph 1.1

2.2 Results

2.2 Dose Response at Different Temperatures

The results listed in the following tables were obtained after a reaction time of 4 hours, at 50% DM:

| | Temperature 34° C. | | | |
|---|---|---|---|---|
| Dose of SEBSoy | Stachyose | Raffinose | Verbascose | Total oligo saccharides |
| Reference | 4.5% | 0.5% | 3.0% | 8.0% |
| 0.05% | 3.5% | 2.0% | 2.5% | 8.0% |
| 0.10% | 3.0% | 3.0% | 2.0% | 8.0% |
| 0.25% | 2.0% | 2.0% | 1.5% | 5.5% |
| 0.50% | 0.5% | 1.5% | 0.5% | 2.5% |

From the results it can be seen that using a 4 hour reaction time at 34° C. require a dose of 0.25% to get a reduction of the total content of oligosaccharides.

| | Temperature 55° C. | | | |
|---|---|---|---|---|
| Dose of SEBSoy | Stachyose | Raffinose | Verbascose | Total oligo saccharides |
| Reference | 4.5% | 0.5% | 3.0% | 8.0% |
| 0.05% | 2.0% | 1.5% | 1.5% | 5.0% |
| 0.10% | 0.5% | 1.5% | 0.5% | 2.5% |
| 0.25% | <0.25% | 0.25% | <0.25% | <0.75% |
| 0.50% | <0.25% | <0.25% | <0.25% | <0.75% |

From the results it can be seen that by using a 4 hour reaction time at 55° C. a dose of only 0.05% is required to get a reduction of the total content of oligosaccharides. This corresponds to an increase in enzymatic activity by a factor about five when the reaction temperature is raised from 34° C. to 55°.

Example 3

Enzymatic Hydrolysis in a Batch Process of a Biomass Comprising Oligosaccharides and Proteins from Soy

3.1 Materials and Methods 200 kg of flash desolventized soy flakes were fed to a closed single bladed worm conveyer able to transport, lift and mix the material. At the same time 170 liter of water and 200 ml of SEBSoy 5.0 L enzyme (0.1% dose of a preparation having an activity of 5,000 α-galactosidase units pr. g of enzyme product) was added to reach a dry matter content of about 50% by weight in the mixture.

The mixture was hydrolyzed for 16 hours at 34° C. and dried to a water content of 5.6%. Watery extracts of the biomass was analyzed for carbohydrate content by the phenol-sulphuric acid method and oligosaccharides were quantified after separation by TLC (Carbohydrate analysis—A practical approach; IRL Press, Oxford. Ed. M. F. Chaplan & J. F. Kennedy, 1986).

3.2 Results

The results are tabulated in the following:

| Subject | Analytical values |
|---|---|
| Protein in DM | 59.6% |
| Soluble carbohydrate | 10.3% |
| Stachyose | <0.25% |
| Raffinose | <0.25% |

From the results it can be seen that a product of the invention has a protein content of about 60% by weight of dry matter and a low content of oligosaccharides.

Example 4

Enzymatic Hydrolysis and Fermentation by Different Yeasts in a Batch Process of a Biomass Comprising Oligosaccharides and Proteins from Soy

4.1 Materials and Methods 200 kg of flash desolventised soy flakes were fed to a closed single bladed worm conveyer able to transport, lift and mix the material. At the same time 170 liter of water and a slurry of spent brewer's yeast or baker's yeast and 200 ml of SEBSoy 5.0 L enzyme (0.1% dose of a preparation having an activity of 5,000 α-galactosidase units pr. g of enzyme product) where added to reach a dry matter content of about 50% by weight in the mixture.

The two mixtures were hydrolyzed for 16 hours at 34° C. and dried to a dry matter content of 95±0.3%.

The product was analyzed as in the previous example.

4.2 Results

The results are tabulated in the following:

| Subject | Analytical values Process with 3.5% spent brewer's yeast added | Analytical values Process with 1.0% baker's yeast Added |
|---|---|---|
| Protein in DM | 62.2% | 61.9% |
| Soluble carbohydrate | 8.2% | 7.2% |
| Stachyose | <0.25 | <0.25% |
| Raffinose | <0.25 | <0.25% |

From the results it can be seen that a product of the invention has a protein content slightly higher than 60% by weight of dry matter when the process is performed under yeast fermentation. The resulting product has a low content of oligosaccharides.

Example 5

Comparative Enzymatic Hydrolysis in a Laboratory Scale Process of a Biomass Comprising Oligosaccharides from Soy In this example the effects on the reduction of oligosaccharides by α-galactosidase under the processing parameters (temperature and dry matter) of the present invention vs. those of WO 2009/143591 is illustrated.

In WO 2009/143591 the water content is claimed to be maximum 35% or better 30% or even better 25%. The optimum temperature for the enzymatic hydrolysis is mentioned to be between 60 and 80° C.

5.1 Materials and Methods

The enzymatic hydrolysis of the oligosaccharides stachyose and raffinose was performed on 10 g of a biomass of defatted soy and full fat soy bean meal and water containing the α-galactosidase enzyme added in an amount to reach a certain dry matter (DM) content of the mixture, and a certain enzyme concentration.

The mixing was performed to ensure homogeneity of the mixture.

The enzymes used in varying concentrations based on the dry matter of defatted soy or of soy bean meal was commercial products available from Advanced Enzyme Technologies, Maharasthra, India, marketed under the trade name SEBSoy, and α-galactosidase from Enzyme Development Corporation (EDC) New York, USA.

The activity of the enzyme preparations was standardised to 5,000 U/g.

The enzymatic hydrolysis was performed in small glass containers at 55° C. or 70° C. for 4 and 16 hours followed by heat treatment at 100° C. to inactivate the enzyme.

After the enzymatic hydrolysis was terminated the content of soluble carbohydrates was extracted by stirring a watery suspension slurry of 10% DM for 30 min followed by centrifugation for 10 min at 3,000×g.

The mono- and oligosaccharide content in the watery extracts of the biomass was analyzed by thin layer chromatography on TLC silica gel 60 plates (Merck). The different components were quantified by comparison to standards of known concentration (*Carbohydrate analysis—A practical approach*; IRL Press, Oxford. Ed. M. F. Chaplan & J. F. Kennedy, 1986).

5.2 Results

A. Present Invention Parameters: DM 45%, Temperature 55° C. and Reaction Time 16 Hours

| Biomass | Enzyme | Stachyose | Raffinose | Stachyose + Raffinose | Oligosaccharide reduction In % |
|---|---|---|---|---|---|
| Defatted soy | — | 6.0% | 3.0% | 9.0% | 0 |
| Defatted soy | 0.05% SEBSoy | <0.25% | 0.75% | <1.0% | >89 |
| Defatted soy | 0.05% EDC | <0.25% | 0.5% | <0.75% | >92 |
| Full fat soy | — | 5.0% | 2.0% | 7.0% | 0 |
| Full fat soy | 0.05% SEBSoy | <0.25% | 0.5% | <0.75% | >89 |
| Full fat soy | 0.05% EDC | <0.25% | <0.25% | <0.5% | >92 |

From the results it can be seen that at the processing parameters of the present invention the reduction of oligosaccharides in the biomass is higher than 89% after a reaction time of 16 hours at an enzyme dose of 0.05%.

B. Present Invention Parameters: DM 45%, Temperature 55° C. and Reaction Time 4 Hours

| Biomass | Enzyme | Stachyose | Raffinose | Stachyose + Raffinose | Oligosaccharide reduction In % |
|---|---|---|---|---|---|
| Defatted soy | — | 6.0% | 3.0% | 9.0% | 0 |
| Defatted soy | 0.25% SEBSoy | <0.25% | <0.25% | <0.5% | >94 |
| Defatted soy | 0.25% EDC | <0.25% | <0.25% | <0.5% | >94 |
| Full fat soy | — | 5.0% | 2.0% | 7.0% | 0 |
| Full fat soy | 0.25% SEBSoy | <0.25% | <0.25% | <0.5% | >93 |
| Full fat soy | 0.25% EDC | <0.25% | <0.25% | <0.5% | >93 |

From the results it can be seen that at the processing parameters of the present invention the reduction of oligosaccharides in the biomass is higher than 93% after a reaction time of 4 hours at an enzyme dose of 0.25%.

C. WO 2009/143591 Parameters: DM 70%, Temperature 70° C. and Reaction Time 4 Hours

| Biomass | Enzyme | Stachyose | Raffinose | Stachyose + Raffinose | Oligosaccharide reduction In % |
|---|---|---|---|---|---|
| Defatted soy | — | 6.0% | 3.0% | 9.0% | 0 |
| Defatted soy | 0.25% SEBSoy | 4.0% | 3.0% | 7.0% | 22 |
| Defatted soy | 0.25% EDC | 2.5% | 3.0% | 5.5% | 39 |
| Full fat soy | — | 5.0% | 2.0% | 7.0% | 0 |
| Full fat soy | 0.25% SEBSoy | 3.0% | 2.5% | 5.5% | 21 |
| Full fat soy | 0.25% EDC | 3.0% | 2.0% | 5.0% | 28 |

From the results it can be seen that at the processing parameters of WO 2009/143591 the reduction of oligosaccharides in the biomass lies in the interval 21-39% after a reaction time of 4 hours at an enzyme dose of 0.25%.

D. WO 2009/143591 Parameters: DM 70%, Temperature 70° C. and Reaction Time 16 Hours

| Biomass | Enzyme | Stachyose | Raffinose | Stachyose + Raffinose | Oligosaccharide reduction In % |
|---|---|---|---|---|---|
| Defatted soy | — | 6.0% | 3.0% | 9.0% | 0 |
| Defatted soy | 0.05% SEBSoy | 6.0% | 3.0% | 9.0% | 0 |
| Defatted soy | 0.05% EDC | 3.5% | 3.0% | 6.5% | 28 |
| Full fat soy | — | 5.0% | 2.0% | 7.0% | 0 |
| Full fat soy | 0.05% SEBSoy | 5.0% | 2.0% | 7.0% | 0 |
| Full fat soy | 0.05% EDC | 4.0% | 2.0% | 6.0% | 14 |

From the results it can be seen that at the processing parameters of WO 2009/143591 the reduction of oligosaccharides in the biomass lies in the interval 0-28% after a reaction time of 16 hours at an enzyme dose of 0.05%.

5.3 Conclusion

From the results it is clear that the processing parameters used in WO 2009/143591 (temperature and dry matter content) are not able to result in the transformation of 80% or more of the oligosaccharides present in a biomass originating from soy; thus it is not possible to attain the same high level of degradation into digestible mono- and disaccharides as can be obtained by the method of the invention.

The invention claimed is:
1. A method for the production of a solid bio-product having a modified sugar profile, comprising:
   (1) reacting an initial mixture of milled or flaked or otherwise disintegrated biomass comprising oligosaccharides and optionally polysaccharides and further comprising proteinaceous plant parts, water, and one or more enzyme preparations containing α-galactosidase(s), for 0.15-36 hours at a temperature of about 20-65° C. under continuous mixing, wherein the initial mixture comprises an amount of said one or more enzyme preparations to provide α-galactosidase(s) in an amount equivalent to from 0.01 to 1.0% by weight, based on the dry matter weight of the biomass, of an α-galactosidase preparation having an activity of 5,000 α-galactosidase units per gram, wherein the amount of the α-galactosidase preparation is effective to convert at least 80% of the original indigestible oligosaccharide content of the biomass into digestible mono- and disaccharides, and wherein the water content in the initial mixture does not exceed 65% by weight of the initial mixture; and (2) incubating the reacted mixture at a temperature and for a time period which inactivate said α-galactosidase(s), thereby obtaining a bio-product having a modified sugar profile, wherein at least 80% of the original indigestible oligosaccharide content of the biomass has been degraded into digestible mono- and disaccharides.

2. The method according to claim 1, further comprising adding fungus and/or bacteria to said biomass in an amount that results in a dry matter ratio of fungus/bacteria to said biomass of from 1:2 to 1:400, wherein said incubating is carried out at a temperature and for a time period which inactivate said α-galactosidase(s) and fungus and/or bacteria.

3. The method according to claim 2, wherein said reacting is performed under anaerobic and/or aerobic conditions.

4. The method according to claim 1, wherein the water content in the initial mixture is from 30 to 65% by weight.

5. The method according to claim 1, wherein said reacting is performed in one or more non-vertical, interconnected paddle worm or continuous worm conveyers with an inlet for the mixture and additives, an outlet for the product, and control(s) for rotation speed, temperature and pH, or in a Vertical Screw Mixer.

6. The method according to claim 5, wherein said continuous worm conveyer is an optionally modified type of a single bladed or multi bladed screw or intersected screw conveyer designed to transport the reacting mixture and at the same time lift the material so that it is transported and agitated without being compacted.

7. A method according to claim 1, wherein the initial mixture further comprises one or more processing aids selected from hop products containing α- and β-acids from hops, or said one or more processing aids is/are added during said reacting.

8. The method according to claim 2, wherein said fungus and/or bacteria is live yeast selected from *Saccharomyces cerevisiae* strains.

9. The method according to claim 1, where said proteinaceous plant parts comprise pulses.

10. The method according to claim 1, where said biomass further comprises oils and fats.

11. The method according to claim 1, where the obtained bio-product is dried to a water content of no more than 10% by weight.

12. The method according to claim 1, where the reacting occurs at 20-55° C.

13. The method according to claim 1, wherein the amount of said α-galactosidase preparation(s) in the initial mixture is equivalent to from 0.25 to 1.0% by weight, based on the dry matter weight of the biomass in the initial mixture, of an α-galactosidase preparation having an activity of 5,000 α-galactosidase units per gram, and said reacting is performed for 4-36 hours at a temperature of 30-60° C.

14. The method according to claim 1, wherein the amount of said α-galactosidase preparation(s) in the initial mixture is equivalent to from 0.25 to 1.0% by weight, based on the dry matter weight of the biomass in the initial mixture, of an α-galactosidase preparation having an activity of 5,000 α-galactosidase units per gram, and said reacting is performed for 4-36 hours at a temperature of 50-60° C.

15. The method according to claim 1, wherein the amount of said α-galactosidase preparation(s) in the initial mixture is equivalent to from 0.01 to 1.0% by weight, based on the dry matter weight of the biomass in the initial mixture, of an α-galactosidase preparation having an activity of 5,000 α-galactosidase units per gram, and said reacting is performed for 8-36 hours at a temperature 50-60° C.

16. The method according to claim 1, wherein the amount of said α-galactosidase preparation(s) in the initial mixture is equivalent to from 0.05 to 1.0% by weight, based on the dry matter weight of the biomass in the initial mixture, of an α-galactosidase preparation having an activity of 5,000 α-galactosidase units per gram, the water content in the initial mixture is from 40-65%, and said reacting is performed at a temperature of 50-60° C.

17. The method according to claim 2, wherein the fungus and/or bacteria is live yeast added in an amount of 0.25% to 10% by weight of the biomass.

18. The method according to claim 1, performed as a batch, fed-batch or continuous process.

19. The method according to claim 8, wherein said fungus and/or bacteria is live yeast selected from the group consisting of spent brewer's yeast, spent distiller's yeast, spent yeast from wine production, baker's yeast, and yeast strains fermenting C5 sugars.

20. The method according to claim 1, where said proteinaceous plant parts comprises proteinaceous plant parts from one or more selected from the group consisting of soy, bean, pea, lupine, cereals, seeds, and grasses, which plant parts optionally may be defatted.

21. The method according to claim 10, where said oils and fats are from seeds of oil bearing plants.

22. The method according to claim 21, where said oil bearing plants are selected from the group consisting of rapeseed and soy.

* * * * *